(12) United States Patent
Black (10) Patent No.: US 7,056,318 B2
(45) Date of Patent: Jun. 6, 2006

(54) TEMPERATURE CONTROLLED HEATING DEVICE AND METHOD TO HEAT A SELECTED AREA OF A BIOLOGICAL BODY

(75) Inventor: Michael Black, Foster City, CA (US)

(73) Assignee: Reliant Technologies, Inc., Mountain View, CA (US)

( * ) Notice: Subject to any disclaimer, the term of this patent is extended or adjusted under 35 U.S.C. 154(b) by 219 days.

(21) Appl. No.: 10/121,236

(22) Filed: Apr. 12, 2002

(65) Prior Publication Data

US 2003/0195592 A1 Oct. 16, 2003

(51) Int. Cl.
*A61B 18/18* (2006.01)

(52) U.S. Cl. .............................. 606/9; 606/17; 607/88; 607/89

(58) Field of Classification Search ................ 606/2, 606/9, 10, 13–17, 41–50; 607/88, 89, 90, 607/92
See application file for complete search history.

(56) References Cited

U.S. PATENT DOCUMENTS

| | | | |
|---|---|---|---|
| 4,646,737 A | | 3/1987 | Hussein et al. .......... 128/303.1 |
| 4,891,043 A | | 1/1990 | Zeimer et al. ................. 604/20 |
| 4,974,587 A | * | 12/1990 | Turner et al. ................ 607/101 |
| 5,057,099 A | * | 10/1991 | Rink ............................ 606/12 |
| 5,225,433 A | | 7/1993 | Dougherty et al. ......... 514/410 |
| 5,334,191 A | * | 8/1994 | Poppas et al. ................. 606/12 |
| 5,662,643 A | * | 9/1997 | Kung et al. ..................... 606/3 |
| 5,766,222 A | * | 6/1998 | Petit ........................... 606/234 |
| 5,810,888 A | * | 9/1998 | Fenn ........................... 607/154 |
| 5,891,187 A | | 4/1999 | Winthrop et al. ............. 607/96 |
| 5,944,748 A | * | 8/1999 | Mager et al. ................. 607/88 |
| 6,074,382 A | * | 6/2000 | Asah et al. ...................... 606/9 |
| 6,099,521 A | * | 8/2000 | Shadduck ....................... 606/4 |
| 6,104,959 A | * | 8/2000 | Spertell ...................... 607/101 |
| 6,113,559 A | | 9/2000 | Klopotek ....................... 601/3 |
| 6,248,727 B1 | | 6/2001 | Zeimer ........................ 514/63 |
| 6,254,598 B1 | * | 7/2001 | Edwards et al. .............. 606/41 |
| 6,273,884 B1 | * | 8/2001 | Altshuler et al. ............... 606/9 |
| 6,325,769 B1 | | 12/2001 | Klopotek ....................... 601/2 |
| 6,440,155 B1 | * | 8/2002 | Matsumae et al. ............ 607/88 |
| 6,443,946 B1 | * | 9/2002 | Clement et al. ................ 606/9 |
| 6,443,978 B1 | * | 9/2002 | Zharov ........................ 607/91 |
| 6,477,426 B1 | * | 11/2002 | Fenn et al. .................. 607/101 |
| 6,514,243 B1 | * | 2/2003 | Eckhouse et al. ............... 606/9 |
| 6,546,934 B1 | * | 4/2003 | Ingle et al. ................... 606/41 |
| 2002/0019625 A1 | * | 2/2002 | Azar ............................. 606/9 |
| 2002/0022829 A1 | * | 2/2002 | Nagase et al. ................ 606/12 |
| 2002/0068926 A1 | * | 6/2002 | Ota et al. ...................... 606/9 |
| 2003/0055414 A1 | * | 3/2003 | Altshuler et al. ............... 606/9 |

\* cited by examiner

*Primary Examiner*—Roy D. Gibson
(74) *Attorney, Agent, or Firm*—Fenwick & West LLP (57) ABSTRACT

A heating device and method are provided that control a temperature in a selected area of a body part to obtain a temperature effect within the selected area for therapeutic or medical purposes. It includes temperature generating means to generate a temperature in the selected area. It also includes temperature detecting means to detect the generated temperature from the selected area. It further includes temperature controlling means to control the temperature generating means to maintain the generated temperature within a range of a desired temperature. The device and method prevent irreversibly damaging or overheating the selected area or the tissue surrounding the selected area. It is advantageous to applications where there is a need to accurately control the temperature in a selected area in a biological body, for instance, to activate or evaporate a temperature sensitive agent in the selected area.

31 Claims, 5 Drawing Sheets

TEMPERATURE CONTROLLED HEATING DEVICE AND METHOD TO HEAT A SELECTED AREA OF A BIOLOGICAL BODY

FIELD OF THE INVENTION

The present invention relates generally to a heating device and method. More particularly, the present invention relates to a heating device and method to increase the temperature in a selected area of a biological body and to control that temperature within a desired temperature range.

BACKGROUND

In general, there are many different medical and therapeutic applications in which heat is applied to the body. For instance, heat is applied to increase the body temperature when a person suffers from hypothermia. Heat is also applied to the body to establish certain temperature effects as they are known in the field of physical therapy and medicine (See for instance, U.S. Pat. No. 5,891,187 to Winthrop et al.).

Recently, photodynamic therapy (PDT) has become popular and encompasses a range of treatments that involve a combination of light and a photo-active chemical agent. This light-activated drug is administered or applied to the patient, followed by illumination with intense light of a specific wavelength matched to the photo-sensitive qualities of the drug. Interaction between the drug and light causes destruction of the target tumor or lesion. Typically, a laser is used as the light source, however, other types of intense light sources may be used in certain dermatological applications.

In U.S. Pat. No. 4,891,043, Zeimer et al. teaches in an application related to PDT that it is necessary for his application to increase the temperature in a particular anatomical locus to approximately 41 degrees Celsius to locally release the content of the liposomes. Zeimer et al. teaches the use of encapsulating drugs inside a liposome, which are not broken unless heated to approximately 41 degrees Celsius. Zeimer et al. teaches that the temperature is accomplished by irradiating the laser light absorbing liposomes at the specific site via a laser beam. Furthermore, Zeimer et al. teaches that it is advantageous to use a argon or krypton laser capable of delivering laser beam pulses with each pulse having a duration of about 200 to about 500 ms.

In U.S. Pat. No. 6,248,727 Zeimer further teaches a first laser beam to selectively heat tissue, including its blood vessels or sinuses, to a temperature of approximately 41 degrees Celcius without causing substantial physiological damage to that tissue or vasculature. A second laser beam is then used to suitably activate a tissue-reactive agent without causing substantial physiological damage to the vasculature in which it is disposed.

In U.S. Pat. No. 5,225,433 Dougherty et al. teaches a treatment in which a photosensitizing drug is injected into a subject. In treating humans or other mammals with the drug, light is irradiated on the tissue in such a position as to uniformly illuminate cancer tissue. Dougherty et al. then further teaches that heat is applied in the range of 40.5 to 45 degrees Celcius. The increase in temperature, accordingly to Dougherty et al., may be achieved by transmitting light: (1) some of which is near or in the infrared spectrum such as at 1060 nm wavelength from a Nd-Yag laser for heat with the light at 630 nm for interaction with the photosensitive drug; or (2) by microwaves such as the 2450 Mhz; or (3) by any other suitable means.

However, in any application where heat is applied to biological tissue during a medical or therapeutic application, irreversible damage to the tissue due to heating, unless intended, should be avoided. Therefore, it is imperative to have feedback from the target area over the temperature. A lack of any type of feedback makes current heating techniques less desirable and difficult to accept in practice. Accordingly, there is a need for advanced heating devices and methods that can be safely used for therapeutic or medical applications.

SUMMARY OF THE INVENTION

The present invention provides a heating device and method that controls a desired temperature in a selected area of a body part. The present invention focuses on obtaining a temperature effect within a selected area which is necessary for therapeutic or medical purposes. The present invention also focuses on either deploying or evaporating a temperature sensitive agent in a selected area by obtaining a desired temperature in the selected area whereby the temperature sensitive agent deploys or evaporates, respectively, at the desired temperature level. The present invention could either be used noninvasively or with an endoscopic means. The present invention includes one or more temperature generating means to generate the desired temperature in the selected area of the biological body. Examples of temperature generating means are, for instance, but not limited to, a light source, RF generator or any type of heating device. The present invention also includes one or more temperature detecting means, such as, but not limited to, infrared measuring devices, to detect the generated temperature from the selected area of the biological body. The present invention further includes one or more temperature controlling means to control the temperature generating means to obtain that the generated temperature is within a range of the desired temperature. The temperature controlling means could include a calculating means to compensate for possible temperature tissue effects that occur between the selected area and the temperature detecting means. Depending on the type of application and also the type of temperature generating means, the present invention could also include a focusing means to focus the radiation generated by a temperature generating means to the selected area. Furthermore, the present invention includes a displaying means to display the generated temperature, for instance, as a suitable qualitative or quantitative measure or graph. In addition, the present invention includes a scanning means to scan over the selected area to generate the desired temperature in the selected area. Accordingly, the present invention also includes a scanning means to scan over the selected area to detect the generated temperature from the selected area.

In view of that which is stated above, it is the objective of the present invention to provide a device and method for noninvasively controlling a desired temperature in a selected area of a biological body.

It is another objective of the present invention to provide device and method for endoscopically controlling a desired temperature in a selected area of a biological body.

It is yet another objective of the present invention to provide a device and method to generate a desired temperature in a selected area of a biological body.

It is still another objective of the present invention to provide a device and method to detect a generated temperature in a selected area of a biological body.

It is still another objective of the present invention to provide a device and method to control the generated temperature in a selected area of a biological body to stay within a range of the desired temperature.

It is still another objective of the present invention to provide a device and method to focus one or more temperature generating beams to one or more selected areas in a biological body.

It is still another objective of the present invention to provide a device and method to deploy a temperature sensitive agent in a selected area of a biological body.

It is still another objective of the present invention to provide a device and method to evaporate a temperature sensitive agent in a selected area of a biological body.

It is another objective of the present invention to provide a device and method to scan over a selected area of a biological body to generate a desired temperature in the selected area.

It is another objective of the present invention to provide a device and method to scan over a selected area of a biological body to detect a generated temperature in the selected area.

The advantage of the present invention over the prior art is that the device and method enables one to safely generate and control a desired temperature in a selected area of a biological body. The device and method of the present invention is advantageous to a variety of applications where there is a need to increase the temperature in a selected area of a biological body for therapeutic or medical purposes. In particular, the present invention is advantageous to PDT applications where there is a need to accurately control the temperature in a selected area to deploy or evaporate a temperature sensitive agent without irreversibly damaging or overheating the selected area or the tissue surrounding the selected area.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a temperature controlled heating device and method to control the temperature of a selected area of a biological body given a desired temperature. The present invention can be used in a variety of medical and therapeutic applications in which it is required to change the temperature of a selected area of a biological body. The present invention could be used to increase the temperature of any selected area such as, but not limited to, cutaneous or subcutaneous tissue, organs, cells, or various anatomical loci or structures. The selected area can be a two-dimensional surface or a three-dimensional shape. The device of the present invention can be a flexible device that can be flexibly placed over the skin or around a body part. The device can be placed against or around, for instance, a breast, a finger, an extremity, part of the belly, or the like. Such a device is characterized as a noninvasive device. However, the present invention is not limited to a noninvasive device and could easily be used as an endoscopic device to heat a selected area while the device has been entered into the body and operates subcutaneous.

The present invention can be used for any type of abnormal or diseased tissue, such as, but not limited to, cancerous tissue. The temperature level can be set to a therapeutic level or at a level that is required for a medical procedure. In some applications, it is important to control the temperature within a few degrees and in other applications less than 1 degree. The present invention can also be used in applications where a temperature sensitive agent (e.g. a chemical agent, dye or the like), that is positioned in a selected area, needs to be deployed or activated and such a deployment only takes place when the selected area is at an increased temperature level. On the other hand, the present invention can be used in applications where a temperature sensitive agent that remained present in a selected area needs to be destroyed, for instance, to prevent potential toxic effects to the tissue or reduce any negative effects of the remained presence of the temperature sensitive agent. The above examples are merely described for illustrative purposes and the present invention should not be limited to these examples.

Figure 1:
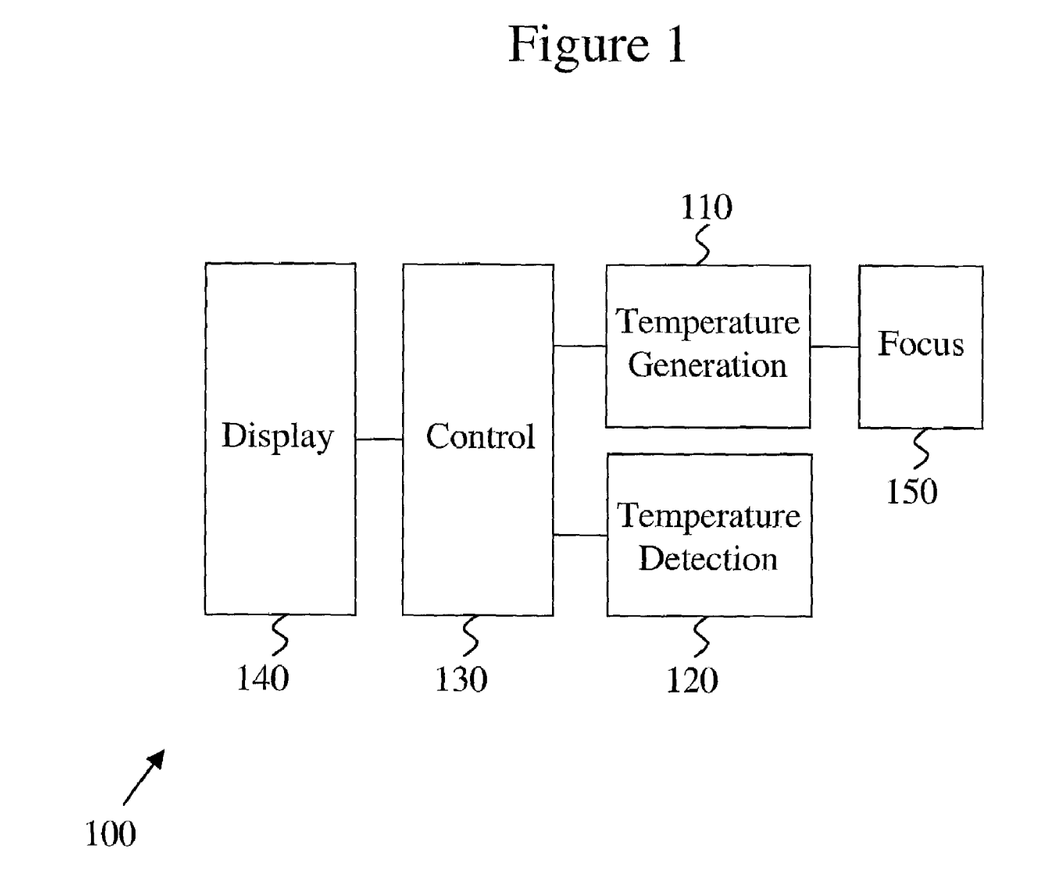
FIG. 1 shows a general example of the device according to the present invention.

FIG. 1 shows an example of a device 100 according to the present invention. Device 100 includes one or more temperature generating means 110, one or more temperature detecting means 120 and one or more temperature controlling means 130. Temperature generating means 110 is able to generate a heating (radiation) beam and increase the temperature of the selected area of a biological body to the desired temperature level. In some applications it would be desirable to generate a uniform temperature field in the selected area. For the purposes of the present invention, uniform is defined as the temperature of the selected area which is more or less the same as the desired temperature and differs only within a certain range or tolerance from the desired temperature. The range or tolerance is dependent on the type of application as one skilled in the art would readily appreciate. As mentioned above, some applications require the desired temperature to stay within a couple degrees, whereas other applications might require the desired temperature to stay within just one degree or even less. Examples of temperature generating means 110 are, for instance, but not limited to, a radio frequency (RF) generator, a light source (such as a laser, a halogen lamp or an arch lamp) or any type of heating device. Temperature generating means 110 should be able to focus the temperature generating beam or radiation beam at the selected area, thereby sometimes passing through various different layers of tissue. Therefore, device 100 could also include a focusing means 150 to focus the radiation from temperature generating means 110 to the selected area. Examples of focusing means 150 are, for instance, but not limited to, any device that is able to focus a radiation beam. In case temperature generating means 110 is a light source, focusing means 150 could be one or more optical lenses and/or mirrors.

Once the heat has been generated and applied to the selected area, the temperature or temperature change in the selected area is detected by temperature detecting means 120. Temperature detecting means 120 detects the temperature of the selected area by sensing the generated temperature from the selected area. Detection could either be accomplished at different time intervals or continuously. However, the type of detection and detection means depends on the specific requirements of the type of therapy or medical intervention. Examples of detection means 120 are, for instance, but not limited to, infrared cameras or infrared thermo-couplers (See, for instance, U.S. Pat. No. 6,219,573 to Exergen Corp.).

These temperature detecting devices come in different models each with a different temperature range, accuracy and spot size, the latter which is also called field of view.

Temperature detecting means 120 provides the necessary information and feedback for temperature controlling means 130 to control the temperature of the selected area within a range of the desired temperature. Temperature controlling means 130 includes hardware and/or software components. Preferably, temperature controlling means 130 includes a software interface so that a user can program and interact with the controller, for instance, to set a specific desired temperature or specify a particular tolerance or range. Temperature controlling means 130 could also include a control function to increase/decrease the temperature to establish the desired temperature. For instance, one could generate a continuous temperature application pattern or any type of discontinuous temperature application pattern. Temperature controlling means 130 could also include various different software programs or modules to calculate and display different parameters or graphs. Furthermore, temperature controlling means 130 includes a calculating means to compensate for possibly temperature tissue effects that generate a temperature gradient over the tissue or bones in between the selected area and the temperature detecting means 120. Examples of a calculating means are, for instance, but not limited to, a look-up table or an equation taking into account temperature tissue effects. Calculating means is usually application specific and could be selected from a control panel or software graphical user interface in temperature controlling means 130. Temperature controlling means 130 could be any type of computer device or chip and is not limited to a particular device. Temperature controlling means 130 is also not limited to the type of software interface or programming language that could be used.

Furthermore, device 100 includes a displaying means 140 to display temperature information obtained from the selected area. Displaying means 140 could be a thermometer (preferably a digital thermometer) or any type of computer display, plotter, printer or graph. Temperature information is, for instance, but not limited to, the temperature or a temperature map of the selected area. As one skilled in the art will readily appreciate, temperature maps could be related to geometrical or anatomical maps (e.g. MRI, CadScan, X-ray or the like).

Figure 2:
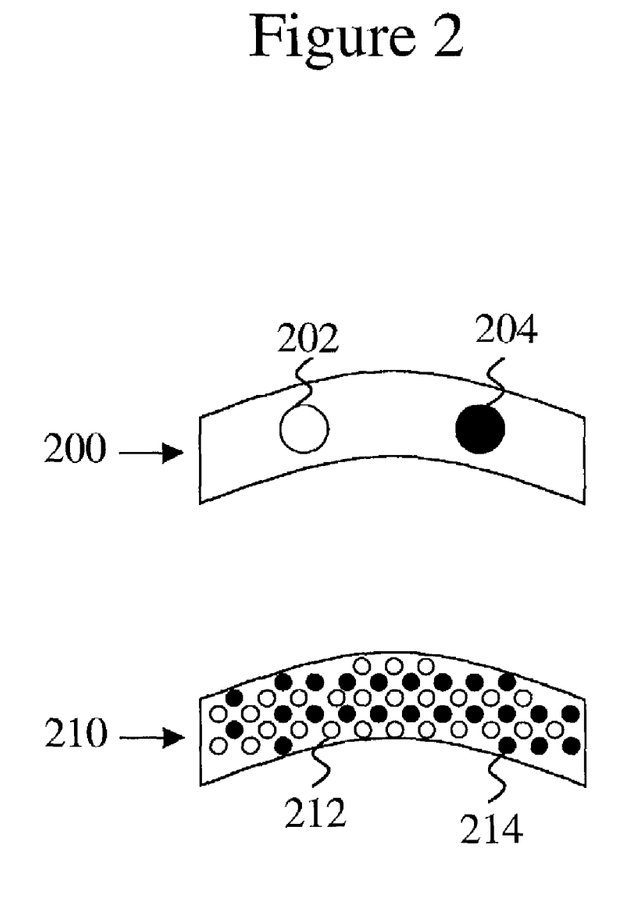
FIG. 2 shows an example of the temperature generating means and temperature detecting means in a device according to the present invention.
Figure 3:
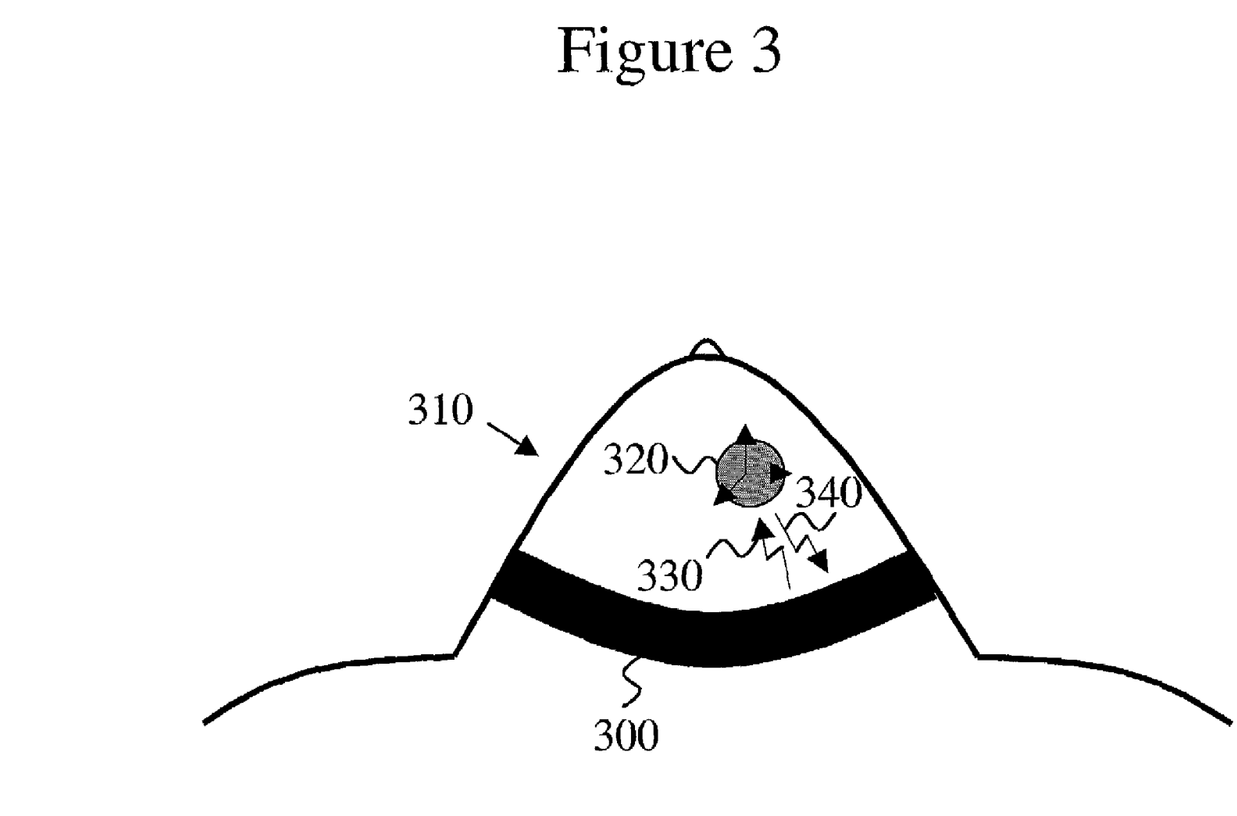
FIG. 3 shows an example of a device flexibly positioned around a breast and a selected area within the breast wherein a desired temperature is generated and detected according to the present invention.

FIG. 2 shows device 200 according to the present invention and includes just one temperature generating means 202 and just one temperature detecting means 204. However, the device of the present invention is not limited to one temperature generating means and one temperature detecting means. Another device 210, according to the present invention, includes a plurality of temperature generating means 212 as well as a plurality of temperature detecting means 214. For purposes of illustration, temperature controlling means, focusing means and displaying means are not shown in FIG. 2 and it should be clear to one skilled in the art that device 200 and 210 could also include one or more temperature controlling means, one or more focusing means and/or one or more displaying means. Device 200 and 210 are displayed as if there were flexibly bent and positioned against a body part as, for instance, shown by device 300 in FIG. 3. FIG. 3 shows device 300 that is placed against (or around) breast 310. Selected area 320 of breast 310 is the target area to be heated by device 300 by temperature generating beam 330. In this particular example, selected area 320 could be an irregular three-dimensional area, such as a lump. In yet another example, a temperature sensitive agent could have been injected into selected area 320 to cure the symptoms or disease in selected area 320. The temperature selected agent will be deployed once it reaches a specific temperature which is usually higher than the body temperature. Temperature detecting beam 340 provides the necessary feedback for device 300 to control the generated temperature at a desired temperature level. For purpose of illustration, only one temperature generating beam and one temperature detection beam is shown in FIG. 3. However, as would be readily appreciated by one skilled in the art, device 300 could include a plurality of temperature generating beams and temperature detecting beams. Furthermore, as would be readily appreciated by one skilled in the art, device 300 could include one or more temperature controlling means, one or more focusing means and/or one or more displaying means.

Figure 4:
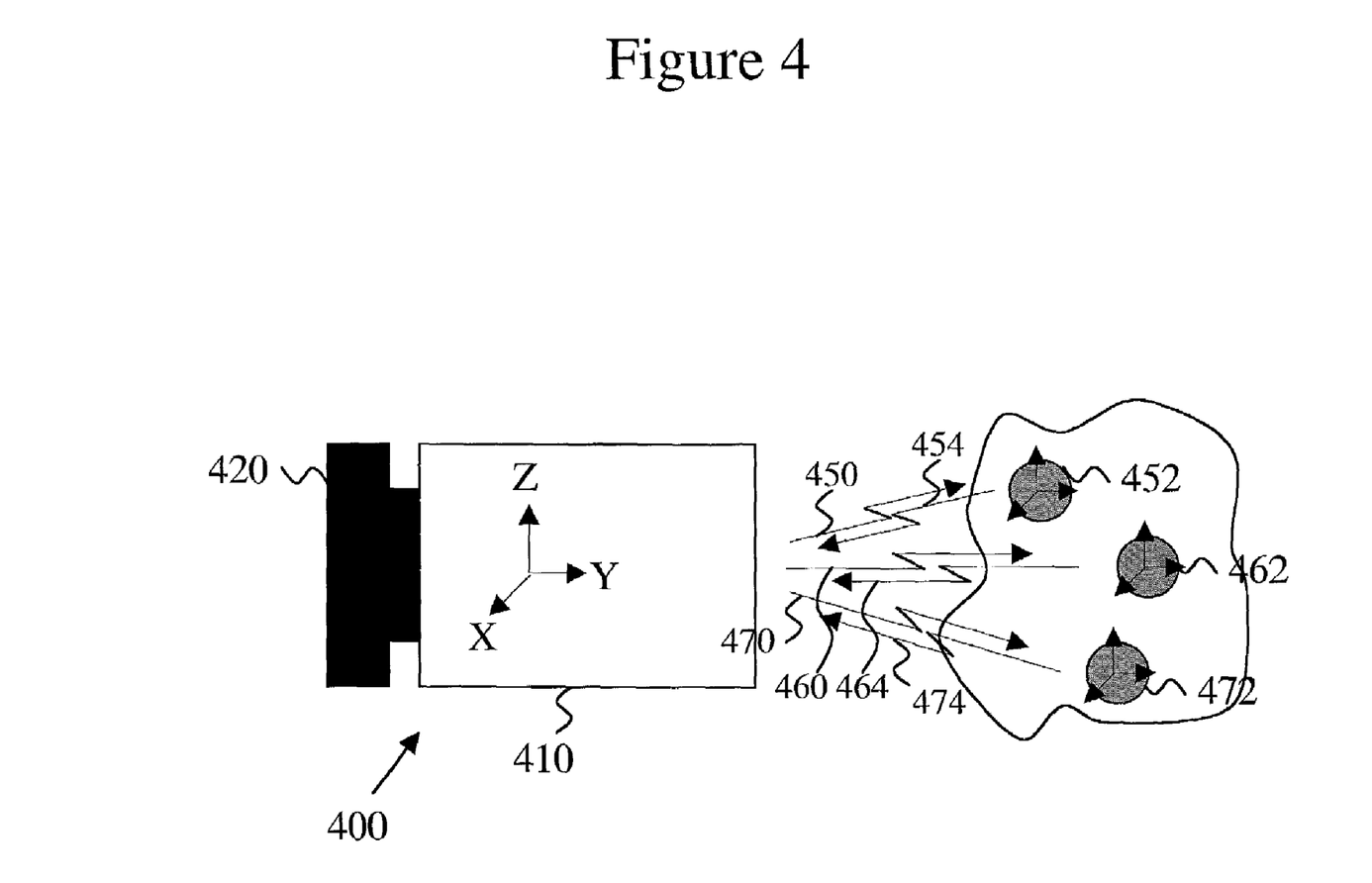
FIG. 4 shows an example of a device with a scanning means to scan over one or more selected areas according to the present invention.

FIG. 4 shows device 400 in which 410 is similar to, for instance, 200 or 210 as shown in FIG. 2. However device 400 now also includes a scanning means 420 to scan over the selected area. Scanning means 420 allows one to scan the temperature generating beam 430 over the selected area. Scanning means 420 also allows one to scan and detect the temperature radiation from various parts of the selected area. Scanning means 420 is helpful when the selected area(s) stretch(es) out over a larger area than the temperature generating means or temperature detecting means could cover. Scanning means 420 is also helpful when the temperature generation is accomplished using different temperature generating means or using a combination of temperature generating means, for instance, to alternate the type of temperature delivery and generation in the selected area. Scanning means 420 could also be helpful to ensure a more uniform temperature generation and detection. Furthermore, scanning means 420 could also be helpful in case a temperature map would be required as discussed above. Scanning means 420 could be any type of means that allows one to rotate and/or translate device 410 in terms of X, Y and Z with respect to the selected area(s) 452, 462 or 472. For instance, temperature generating beams 450, 460 and 470 target selected area 452, 462 and 472, respectively. Accordingly, temperature detecting beams 454, 464 and 474 detect selected area 452, 462 and 472, respectively. Scanning means 420 could be accomplished by, for instance, but not limited to, a hand of a user, one or more translation bars or rotation joints, one or more linear or rotary motors, or a combination thereof. As one skilled in the art would readily appreciate, each individual temperature generating means and/or temperature detecting means could have its own scanning means so that they could be individually steered and controlled over the selected area(s). However, the present invention could also include one single scanning means to steer one or more temperature generating means and/or temperature detecting means at the same time.

Figure 5:
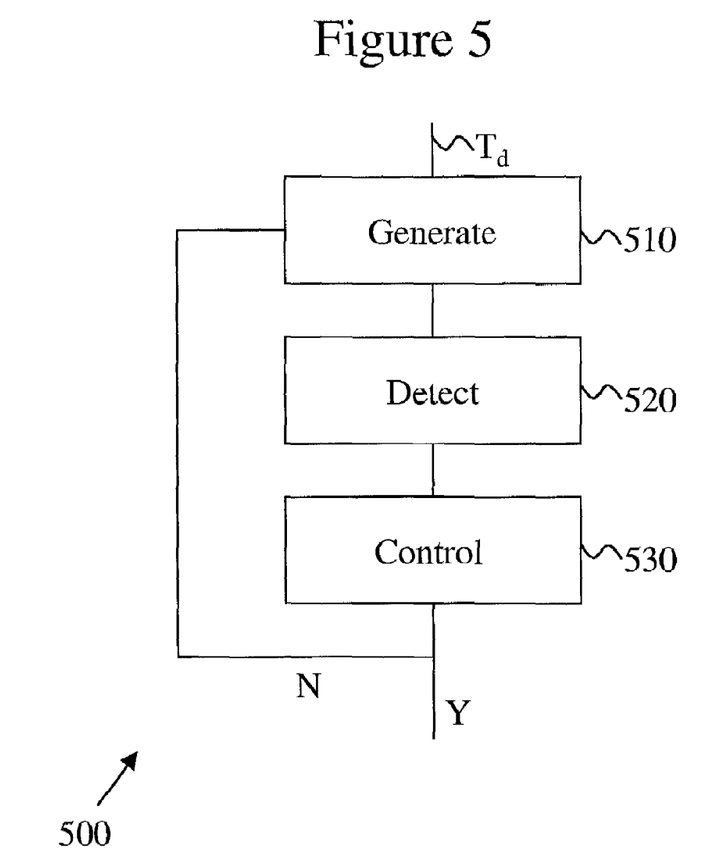
FIG. 5 shows a general overview of the method according to the present invention.

FIG. 5 shows a general overview of the method 500 according to the present invention which could be accomplished noninvasively or by an endoscopic means as discussed above. The method includes the step of generating 510 a desired temperature $T_d$ in a selected area of a biological body part using a temperature generating means. Once the step of generating has been initialized, the method further includes the step of detecting 520 the generated temperature in the selected area using as temperature detecting means. Using the detected temperature, the method further includes the step of controlling 530 the temperature generating means to obtain that the generated temperature stays within a desired range. Therefore if the temperature is within the desired range—indicated by Y—then no further action or adjustment is needed, whereas if the temperature is not within the desired range—indicated by N—then appropriate action or adjustment is required. This adjustment could either be a decrease, when the detected temperature is higher than the desired temperature, or increase when the temperature is lower than the desired temperature. In conjunction to the device as discussed above, the method of the present invention could also include the step of focusing the radiation generated by the temperature generating means to the selected area. Furthermore the present invention optionally includes step of compensating for temperature tissue effects using a calculating means. The method could also include step of providing a scanning means to scan over the selected area to generate the desired temperate in the selected area as well as step of providing a scanning means to scan over the selected area to detect the generated temperature from the selected area. Finally, the method includes the step of displaying any type of data or graphs that is obtained from the selected area. The data or graphs could have been calculated using a calculating means such as, but not limited to, a computer program.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, the device of the present invention could also be arranged as an array of devices to target multiple selected areas. All such variations are considered to be within the scope and spirit of the present invention as defined by the following claims and their legal equivalents.

What is claimed is:

1. A device for noninvasively controlling a temperature in a selected area of a biological body, comprising:
   (a) at least one temperature generating means to generate a temperature in said selected area of said biological body, wherein said at least one temperature generating means comprises a scanning means to scan a radiation generated by said at least one temperature generating means over said selected area of said biological body, wherein said at least one temperature generating means further comprises a light source, wherein said light source is one of a halogen lamp, a laser, and an arc lamp;
   (b) at least one temperature detecting means to detect said generated temperature from said selected area of said biological body; and
   (c) at least one temperature controlling means to control said at least one temperature generating means to maintain said generated temperature within a range of a desired temperature, wherein said at least one temperature controlling means comprises a calculating means to compensate for temperature tissue effects.

2. A device for noninvasively controlling a temperature in a selected area of a biological body, comprising:
   (a) at least one temperature generating means to generate a temperature in said selected area of said biological body, wherein said at least one temperature generating means comprises a scanning means to scan a radiation generated by said at least one temperature generating means over said selected area of said biological body;
   (b) at least one temperature detecting means to detect said generated temperature from said selected area of said biological body;
   (c) at least one temperature controlling means to control said at least one temperature generating means to maintain said generated temperature within a range of a desired temperature, wherein said at least one temperature controlling means comprises a calculating means to compensate for temperature tissue effects; and
   (d) at least one focusing means to focus said radiation generated by said at least one temperature generating means to said selected area of said biological body.

3. The device as set forth in claim 2 wherein said desired temperature is above a normal body temperature.

4. The device as set forth in claim 2 wherein said generated temperature is maintained within less than 1° C. of said desired temperature.

5. The device as set forth in claim 2, wherein said desired temperature activates a temperature sensitive agent in said selected area, wherein said desired temperature is above a normal body temperature.

6. The device as set forth in claim 2, wherein said desired temperature evaporates a temperature sensitive agent in said selected area, wherein said desired temperature is above a normal body temperature.

7. The device as set forth in claim 2, wherein said at least one temperature detecting means comprises at least one infrared measuring device.

8. The device as set forth in claim 2, further comprising at least one displaying means to display said generated temperature.

9. The device as set forth in claim 2, wherein said device is a flexible device that comfortably fits to a body part.

10. A method for noninvasively controlling a temperature in a selected area of a biological body, comprising:
    (a) generating a temperature in said selected area of said biological body with at least one temperature generating means;
    (b) providing a scanning means to scan a radiation generated by said at least one temperature generating means over said selected area of said biological body;
    (c) detecting said generated temperature from said selected area of said biological body with at least one temperature detecting means; and
    (d) controlling said at least one temperature generating means to maintain said generated temperature within a range of a desired temperature with at least one temperature controlling means, wherein controlling said at least one temperature generating means comprises compensating for temperature tissue effects.

11. The method as set forth in claim 10, further comprising displaying said generated temperature.

12. The method as set forth in claim 10, wherein detecting said generated temperature comprises scanning over said selected area of said biological body to detect said generated temperature from said selected area of said biological body.

13. An endoscopic device for controlling a temperature in a selected area of a biological body, comprising:
(a) at least one temperature generating means to generate a temperature in said selected area of said biological body, wherein said at least one temperature generating means comprises a scanning means to scan a radiation generated by said at least one temperature generating means over said selected area of said biological body, wherein said at least one temperature generating means further comprises a light source;
(b) at least one temperature detecting means to detect said generated temperature from said selected area of said biological body, wherein said at least one temperature detecting means comprises at least one infrared measuring device; and
(c) at least one temperature controlling means to facilitate selection of a desired temperature and to control said at least one temperature generating means to maintain said generated temperature within less than 1° C. of said desired temperature.

14. The endoscopic device as set forth in claim 13, wherein said light source is one of a halogen lamp, a laser, and an arc lamp.

15. The endoscopic device as set forth in claim 13, wherein said at least one temperature generating means further comprises a RE generator.

16. The endoscopic device as set forth in claim 13, wherein said desired temperature is above a normal body temperature.

17. The endoscopic device as set forth in claim 13, wherein said desired temperature activates a temperature sensitive agent in said selected area, wherein said desired temperature is above a normal body temperature.

18. The endoscopic device as set forth in claim 13, wherein said desired temperature evaporates a temperature sensitive agent in said selected area, wherein said desired temperature is above a normal body temperature.

19. The endoscopic device as set forth in claim 13, further comprising at least one displaying means to display said generated temperature.

20. The endoscopic device as set forth in claim 13, wherein said at least one temperature detecting means further comprises a scanning means to scan over said selected area of said biological body to detect said generated temperature from said selected area of said biological body.

21. An endoscopic device for controlling a temperature in a selected area of a biological body, comprising:
(a) at least one temperature generating means to generate a temperature in said selected area of said biological body, wherein said at least one temperature generating means comprises a scanning means to scan a radiation generated by said at least one temperature generating means over said selected area of said biological body;
(b) at least one temperature detecting means to detect said generated temperature from said selected area of said biological body, wherein said at least one temperature detecting means comprises at least one infrared measuring device;
(c) at least one temperature controlling means to facilitate selection of a desired temperature and to control said at least one temperature generating means to maintain said generated temperature within less than 1° C. of said desired temperature; and (d) at least one focusing means to focus a radiation generated by said at least one temperature generating means to said selected area of said biological body.

22. A method for endoscopically controlling a temperature in a selected area of a biological body, comprising:
(a) facilitating selection of a desired temperature range with at least one temperature controlling means;
(b) generating a temperature in said selected area of said biological body with at least one temperature generating means, wherein said at least one temperature generating means comprises a light source;
(c) providing a scanning means to scan a radiation generated by said at least one temperature generating means over said selected area of said biological body;
(d) detecting said generated temperature from said selected area of said biological body with at least one temperature detecting means; and
(e) controlling said at least one temperature generating means to maintain said generated temperature within said desired temperature range with said at least one temperature controlling means.

23. The method as set forth in claim 22, further comprising focusing a radiation generated by said at least one temperature generating means to said selected area of said biological body.

24. The method as set forth in claim 22, wherein controlling said at least one temperature generating means comprises compensating for temperature tissue effects.

25. The method as set forth in claim 22, further comprising displaying said generated temperature.

26. The method as set forth in claim 22, wherein detecting said generated temperature comprises scanning over said selected area of said biological body to detect said generated temperature from said selected area of said biological body.

27. A device for evaporating a temperature sensitive agent in a selected area of a biological body by controlling a temperature in said selected area of said biological body, comprising:
(a) at least one temperature generating means to generate a temperature in said selected area of said biological body;
(b) at least one temperature detecting means to detect said generated temperature from said selected area of said biological body, wherein said at least one temperature detecting means comprises a scanning means to scan over said selected area of said biological body to detect said generated temperature; and
(c) at least one temperature controlling means to control said at least one temperature generating means to maintain said generated temperature within a range of a desired temperature, wherein said desired temperature evaporates said temperature sensitive agent, and wherein said at least one temperature controlling means comprises a calculating means to compensate for temperature tissue effects.

28. The device as set forth in claim 27, wherein said device is a noninvasive device.

29. The device as set forth in claim 27, wherein said device is configured for endoscopic use.

30. A method for evaporating a temperature sensitive agent in a selected area of a biological body by controlling a temperature in said selected area of said biological body, comprising:
(a) providing said temperature sensitive agent in said selected area of said biological body;

(b) facilitating selection of a desired temperature that evaporates said temperature sensitive agent with at least one temperature controlling means;
(c) generating a temperature in said selected area of said biological body with at least one temperature generating means;
(d) detecting said generated temperature from said selected area of said biological body with at least one temperature detecting means; and
(e) controlling said temperature generating means to obtain said generated temperature within a range of said desired temperature with said at least one temperature controlling means.

31. A device for noninvasively controlling a temperature in a selected area of a biological body, comprising:
(a) at least one temperature generating means to generate a temperature in said selected area of said biological body, wherein said at least one temperature generating means comprises a scanning means to scan a radiation generated by said at least one temperature generating means over said selected area of said biological body, wherein said at least one temperature generating means further comprises a RF generator;
(b) at least one temperature detecting means to detect said generated temperature from said selected area of said biological body; and
(c) at least one temperature controlling means to control said at least one temperature generating means to maintain said generated temperature within a range of a desired temperature, wherein said at least one temperature controlling means comprises a calculating means to compensate for temperature tissue effects.

* * * * *

UNITED STATES PATENT AND TRADEMARK OFFICE
CERTIFICATE OF CORRECTION

| | | |
|---|---|---|
| PATENT NO. | : 7,056,318 B2 | Page 1 of 1 |
| APPLICATION NO. | : 10/121236 | |
| DATED | : June 6, 2006 | |
| INVENTOR(S) | : Black | |

It is certified that error appears in the above-identified patent and that said Letters Patent is hereby corrected as shown below:

Column 9,
Line 29, please replace "RE" with -- RF --.

Signed and Sealed this

First Day of August, 2006

JON W. DUDAS
*Director of the United States Patent and Trademark Office*